US007844100B2

(12) United States Patent
Auerbach

(10) Patent No.: US 7,844,100 B2
(45) Date of Patent: Nov. 30, 2010

(54) METHOD FOR FILTERING NUISANCE DEFECTS

(75) Inventor: Ditza Auerbach, Aseret (IL)

(73) Assignee: Applied Materials Israel, Ltd., Rehovot (IL)

( * ) Notice: Subject to any disclaimer, the term of this patent is extended or adjusted under 35 U.S.C. 154(b) by 1015 days.

(21) Appl. No.: 11/287,815

(22) Filed: Nov. 28, 2005

(65) Prior Publication Data

US 2006/0115143 A1    Jun. 1, 2006

Related U.S. Application Data

(60) Provisional application No. 60/631,912, filed on Nov. 29, 2004.

(51) Int. Cl.
*G06K 9/00* (2006.01)
(52) U.S. Cl. .................................. 382/145; 382/150
(58) Field of Classification Search ................. 382/144, 382/145, 149, 172
See application file for complete search history.

(56) References Cited

U.S. PATENT DOCUMENTS

| | | | | |
|---|---|---|---|---|
| 5,265,200 A * | 11/1993 | Edgar | ........................... | 345/589 |
| 5,619,429 A * | 4/1997 | Aloni et al. | .................. | 700/279 |
| 5,966,459 A | 10/1999 | Chen et al. | | |
| 5,978,501 A | 11/1999 | Badger et al. | | |
| 5,991,699 A * | 11/1999 | Kulkarni et al. | ............... | 702/83 |
| 6,256,093 B1 * | 7/2001 | Ravid et al. | .............. | 356/237.2 |
| 6,297,879 B1 * | 10/2001 | Yang et al. | ................ | 356/237.5 |
| 6,466,895 B1 * | 10/2002 | Harvey et al. | ................ | 702/181 |
| 6,483,938 B1 * | 11/2002 | Hennessey et al. | .......... | 382/149 |
| 6,487,307 B1 | 11/2002 | Hennessey et al. | | |
| 6,701,004 B1 | 3/2004 | Shykind et al. | | |
| 7,263,208 B1 * | 8/2007 | Crosby et al. | ................ | 382/103 |
| 7,508,973 B2 * | 3/2009 | Okabe et al. | ................. | 382/145 |
| 2002/0181756 A1 * | 12/2002 | Shibuya et al. | ............... | 382/145 |
| 2003/0174878 A1 * | 9/2003 | Levin et al. | .................. | 382/149 |
| 2004/0028276 A1 | 2/2004 | Okuda et al. | | |
| 2004/0218806 A1 * | 11/2004 | Miyamoto et al. | ........... | 382/145 |
| 2006/0265145 A1 * | 11/2006 | Huet et al. | ..................... | 702/35 |

OTHER PUBLICATIONS

The Clustering algorithm—defects into clusters, INSPEC, Zhao et al. 0007421260, Jun. 2002, abstract.*
D. Auerbach, Method for filetering nuisance defects, U.S. Appl. No. 60/631,912, filed Nov. 29, 2004, 21 pp.

* cited by examiner

*Primary Examiner*—Samir A. Ahmed
*Assistant Examiner*—Jayesh Patel
(74) *Attorney, Agent, or Firm*—SNR Denton US LLP

(57) ABSTRACT

A method for inspecting a sample, consisting of receiving a definition of image attributes that are characteristic of defects, and processing an image of the sample so as to identify candidate defects on the sample. The method further includes forming distributions of values of the respective attributes from the candidate defects, and selecting a set of the candidate defects that are characterized by respective candidate attribute values that fall in one or more tails of the distributions. The selected set is presented to a human operator, and respective classifications of the candidate defects in the selected set are received from the operator. A definition of the one or more tails of the distributions is refined responsively to the classifications. The method may be used as a filter to remove false alarms, or nuisances. The method may also be used to categorize the candidate defects into two or more classes.

30 Claims, 4 Drawing Sheets

METHOD FOR FILTERING NUISANCE DEFECTS

CROSS-REFERENCE TO RELATED APPLICATION

This application claims the benefit of U.S. Provisional Patent Application 60/631,912, filed Nov. 29, 2004, which is incorporated herein by reference.

FIELD OF THE INVENTION

The present invention relates generally to semiconductor wafer fabrication, and specifically to detecting defects in the fabricated wafer.

BACKGROUND OF THE INVENTION

An integral part of semiconductor wafer fabrication is detection of defects that lead to reduced performance of the die where the defect is located. A number of methods for performing such detection are known in the art. The methods usually include optical and/or charged particle scanning of the wafer, and analysis of the scanned image. One of the methods for detecting defects uses comparison of the image with other images, typically on a die-to-die basis and/or on a wafer-to-wafer basis, so that regions of the wafer which may have defects can be identified. Other methods are known in the art.

One of the problems of defect identification is that identified defects may in fact not lead to reduced performance of the die. For example, the existence of metal grains in the die, of a rough edge on a conductor, or of anomalies under a scanned layer, typically do not reduce performance. It is thus useful to classify defects, and to use the classification to reduce the number of defects which are considered problematic.

U.S. Pat. No. 5,966,459 to Chen, et al., whose disclosure is incorporated herein by reference, describes a method for determining classification codes for semiconductor wafer defects, and for storing the information used to determine the classification codes. A wafer is scanned after a first and subsequent manufacturing processes. After each scan images of selected defects of the wafer are examined, and are assigned a code. The code is modified according to the results of the subsequent scans.

U.S. Pat. No. 5,978,501 to Badger, et al., whose disclosure is incorporated herein by reference, describes a system for detecting defects in the design of a photolithographic mask or of a semiconductor wafer. The system derives an adaptive inspection algorithm that is claimed to allow for a tighter inspection of a mask or a wafer to a data set which has repeatable differences. The inspection is also claimed to allow flexibility in removal of unimportant differences while maintaining a tight inspection capability.

U.S. Pat. No. 6,483,938 to Hennessey, et al., whose disclosure is incorporated herein by reference, describes a system for generating a knowledge base for use in labeling anomalies on a manufactured object. A pixel-based representation of an image having an anomaly is decomposed into primitives. The anomaly is isolated, and is compared with primitives of known anomalies to locate the closest primitive set. A label of the set is presented to an operator using the system.

U.S. Pat. No. 6,487,307 to Hennessey, et al., whose disclosure is incorporated herein by reference, describes a system for optically inspecting structures on an object on a moving platform. Structure edges within the object are delineated, and a sequence of images of the object are captured. The structure is detected in each image, and a histogram is produced for each image identifying the slope and length of each edge of the structure. The histograms are used to reduce differences between images and are claimed to be able to detect foreign objects and other defects in the object.

U.S. Pat. No. 6,701,004 to Shykind, et al., whose disclosure is incorporated herein by reference, describes a method for detecting defects on a photomask by patterning alternating dice on a wafer with different process conditions. The different conditions, such as a length of exposure time and an optical focus condition, are configured to highlight and detect defect areas.

U.S. Patent Application 2004/0028276 to Okuda, et al., whose disclosure is incorporated herein by reference, describes an automatic defect classifying system. A user defines a classifying class arrangement by combining classes supplied by the system itself or classes defined by the user. The user also provides the system with a priori knowledge on the defect class, the knowledge being used as a restriction so as to carry out restricted learning.

SUMMARY OF THE INVENTION

In embodiments of the present invention, a wafer inspection system generates a set of defects of the wafer, and the system performs an initial filtration of the defects to generate candidate defects for further analysis. The inspection system generates values of image attributes for each of the candidate defects, the image attributes typically comprising expressions that are functions of measurements of the candidate defects made by the inspection system. The image attributes may be generated from one or more signals from the candidate defects.

The inspection system forms distributions of each of the image attributes of the candidate defects, and selects candidate defects that are in tails of the distributions. The tails are defined by threshold values for the attribute distributions. The candidate defects that are in the tails are presented to a human operator in the form of a display on a monitor, and the operator classifies the presented defects as true defects or as false alarms, also herein termed nuisances.

The inspection system uses the classifications of the operator to refine the values of the thresholds of the attribute distributions, typically in an iterative manner, until a required false alarm rate (FAR), also herein termed a nuisance rate, of classified defects is achieved by the threshold values.

In an embodiment of the invention, a further modification of the threshold values is performed by analyzing correlations between the attribute values of defects lying in attribute tails.

The present invention will be more fully understood from the following detailed description of the embodiments thereof, taken together with the drawings, a brief description of which follows.

DETAILED DESCRIPTION OF EMBODIMENTS

Figure 1:
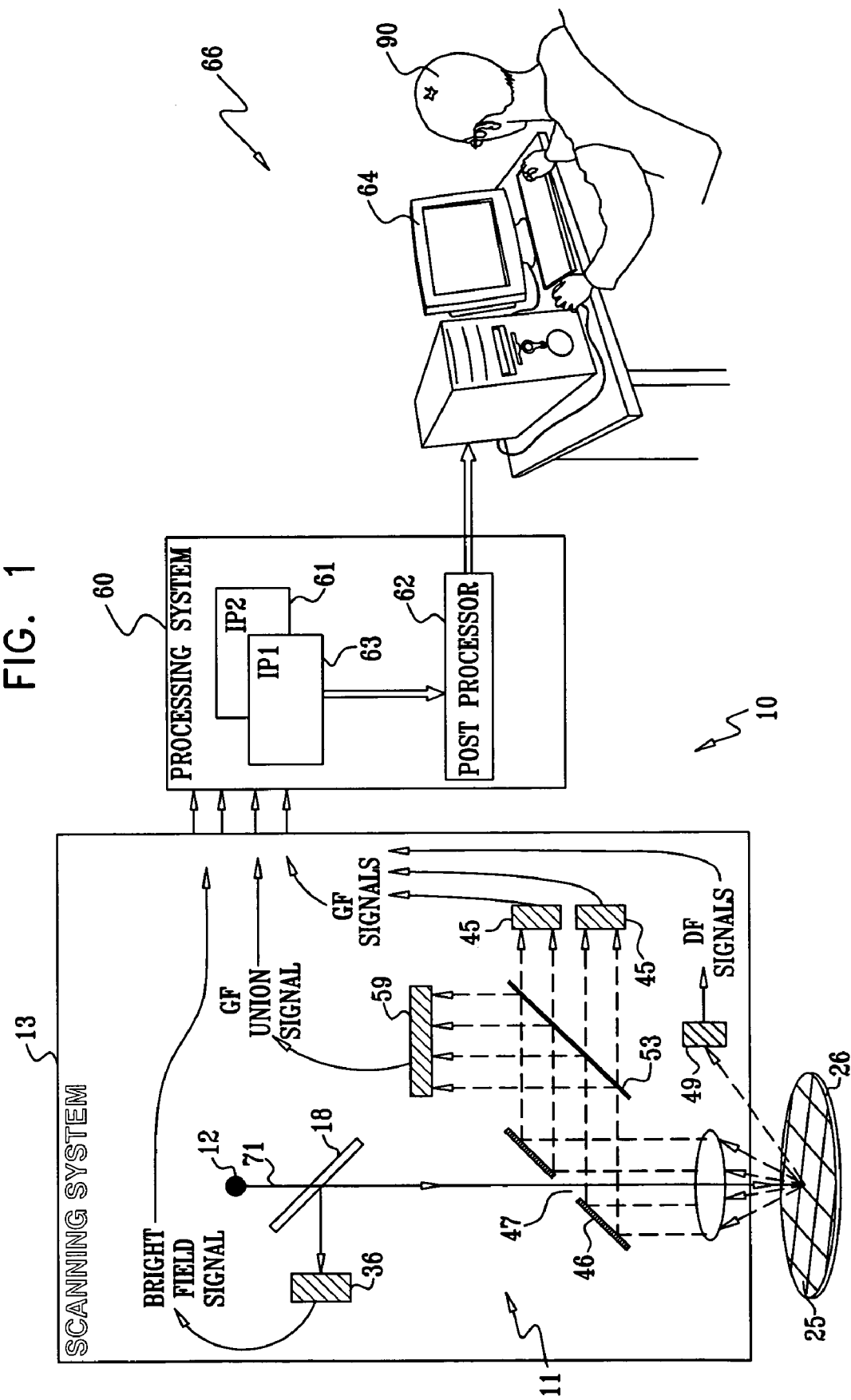
FIG. 1 is a schematic illustration of a wafer inspection apparatus, according to an embodiment of the present invention.

Reference is now made to FIG. 1, which is a schematic illustration of a wafer inspection apparatus 10, according to an embodiment of the present invention. Apparatus 10 is used to inspect a surface 25 of a wafer 26, typically a semiconductor wafer, during one or more stages of fabrication of the wafer. Herein, by way of example, apparatus 10 is assumed to use an optical inspection scanning system 13, but those having ordinary skill in the art will be able, mutatis mutandis, to adapt the following description to accommodate other inspection systems or combinations of inspection systems. Such systems include, but are not limited to, inspection of wafer 26 by substantially any type of electromagnetic radiation and/or charged particle scanning.

Apparatus 10 comprises a source 12, typically a laser, which radiates an optical beam 71 onto surface 25. Reflected and/or scattered light that results from the irradiation is detected in a number of detectors 11. Herein detectors 11 are assumed to comprise a bright field detector 36, which receives specular reflection from surface 25 via a partially reflecting element 18. Detectors 11 also comprise four generally similar gray field (GF) detectors 45 (for clarity, only two of the GF detectors are shown in FIG. 1), which receive near field scattered radiation from surface 25 via a mirror 46 and a partially reflecting element 53. Mirror 46 has a hole 47 in its center to allow beam 71 to have unimpeded access to surface 25, as well as to allow specular reflection of the beam to be received by detector 36. The four detectors 45 are arranged substantially symmetrically around beam 71, so that each detector receives radiation scattered into different but approximately equal solid angles with respect to surface 25. A fifth gray field detector 59, herein termed the gray field union (GFU) detector, receives scattered radiation, via element 53, corresponding to a sum of the individual radiations received by detectors 45.

Detectors 11 also comprise a number, typically four, of dark field detectors 49 which receive far field scattered radiation from surface 25. For clarity, only one dark field detector is shown in FIG. 1.

Apparatus 10 further comprises processing system 60 and a computing system 66 including a monitor 64. Processing system 60 comprises two image processors (IPs) 61 and 63, also referred to herein as IP1 and IP2 respectively, and a post-processor 62. As shown in FIG. 1, processing system 60 receives respective signals from each of detectors 11. The functions of systems 60 and 66 are described in more detail below with respect to FIG. 2.

Apparatus 10 inspects surface 25 in order to locate defects on or close to the surface. By way of example, the inspection process is assumed to comprise a die-to-die comparison, although other inspection processes known in the art, such as a wafer-to-wafer comparison and/or comparison with results from a database, may also be used. The defects that are identified by the inspection process, prior to any filtering, typically comprise large numbers of defects that have little or no effect on the performance of the die to which the defect belongs, these type of defects being non-yield-limiting defects. Typical non-yield-limiting defects include metal grains and irregular edges of conductors in a die. Embodiments of the present invention enable the defects to be filtered so that only those defects with a high probability of limiting the yield are identified; these defects are herein termed true defects. Other defects, also herein termed false alarms, nuisance defects, or nuisances, are filtered out.

Apparatus 10 is typically operated in an initial "learning" phase, and subsequently in a production phase. In the learning phase, surface 25 of wafer 26 is inspected, and a human operator 90 of apparatus 10 interacts with the apparatus, using results generated by the apparatus, to iteratively decide values of the results that have a high probability of being generated by yield limiting defects. In the production phase, surfaces of other wafers are inspected, these wafers being in substantially the same phase of fabrication as already-inspected wafer 26. The production phase inspection uses the learning phase results derived from the inspection of wafer 26. As a consequence, during the production phase the values determined in the learning phase enable apparatus 10 to automatically filter out nuisance defects.

Figure 2:
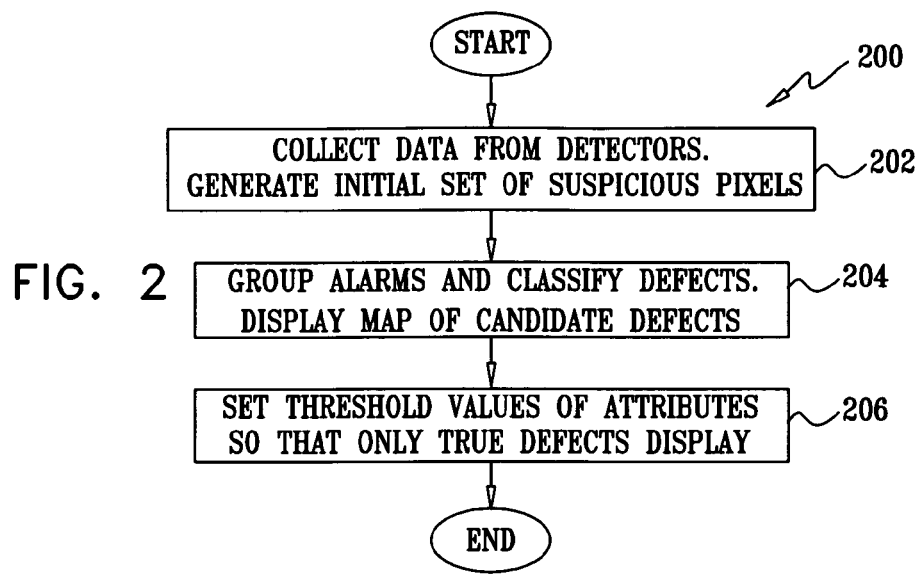
FIG. 2 is a flowchart showing an overall inspection process performed by the wafer inspection apparatus, according to an embodiment of the present invention.

FIG. 2 is a flowchart showing an overall inspection process 200 performed by apparatus 10, according to an embodiment of the present invention. Process 200 includes the learning phase referred to above. In a first step 202, typically performed as beam 71 is scanned across surface 25, data from detectors 11 is passed to image processors 61 and 63. For each detector 11, processors 61 and 63 compare the level from the detector with the level from the same detector for corresponding pixels of neighboring dies. From the comparisons generated processors 61 and 63 generate an initial set of suspicious pixels; suspicious pixels are also referred to herein as alarms.

In a second step 204, typically performed in post-processor 62 after surface 25 has been completely scanned, the alarms are grouped into clusters, and the clusters are classified as defects. Typically one cluster represents one defect. Post-processor 62 performs further filtering of each of the defects according to the properties of each defect, where the properties comprise the number of alarms, also herein termed the volume, in the cluster, and its grade, which is a function of individual alarm grades of each alarm. Defects clustered by the post-processor and not filtered are displayed as a candidate defect map on monitor 64.

In a third step 206, operator 90 may use the displayed map of candidate defects produced in step 204 to adjust threshold values of parameters, herein termed attributes, associated with the candidate defects so that some of these defects are classified as nuisances. The initial threshold values are generated automatically by post-processor 62. The attributes are derived from the volume and grade of the defect, as well as from additional parameters associated with the defects. The attributes, and the setting of the threshold values of the attributes, are described in more detail below with reference to FIGS. 4 and 5; the setting of the threshold values of the attributes comprises the learning phase performed by apparatus 10. When operator 90 has verified that the threshold values of the attributes display substantially only true defects on monitor 64, process 200 concludes.

It will be appreciated that the map of candidate defects generated after step 204, and displayed on monitor 64, may typically comprise an extremely large proportion of nuisance defects. The learning phase provided by step 206 reduces the numbers of nuisance defects displayed, using assumptions that are described below with reference to FIGS. 3A, 3B, and 4.

Figure 3A:
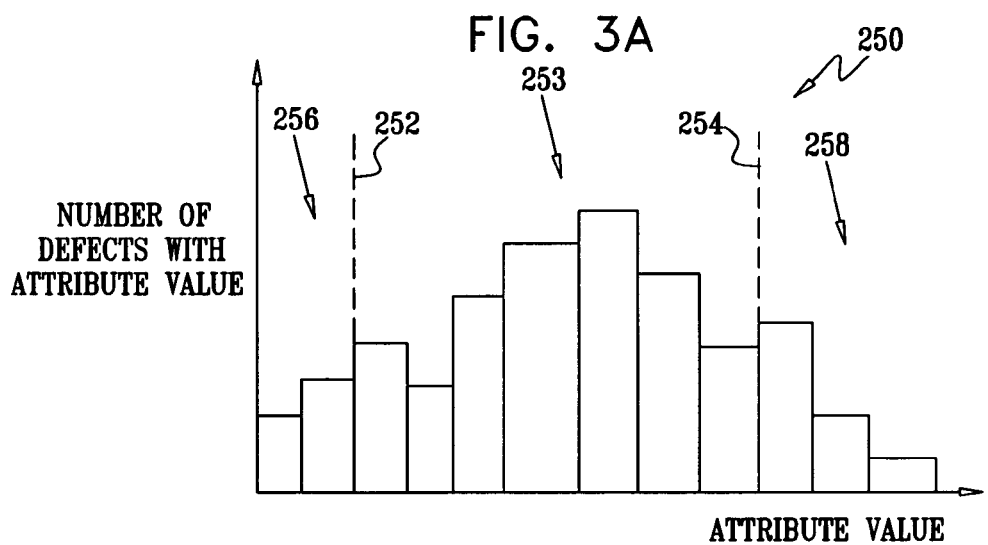
FIGS. 3A and 3B are schematic histograms of a generic attribute of defects, according to an embodiment of the present invention.
Figure 3B:
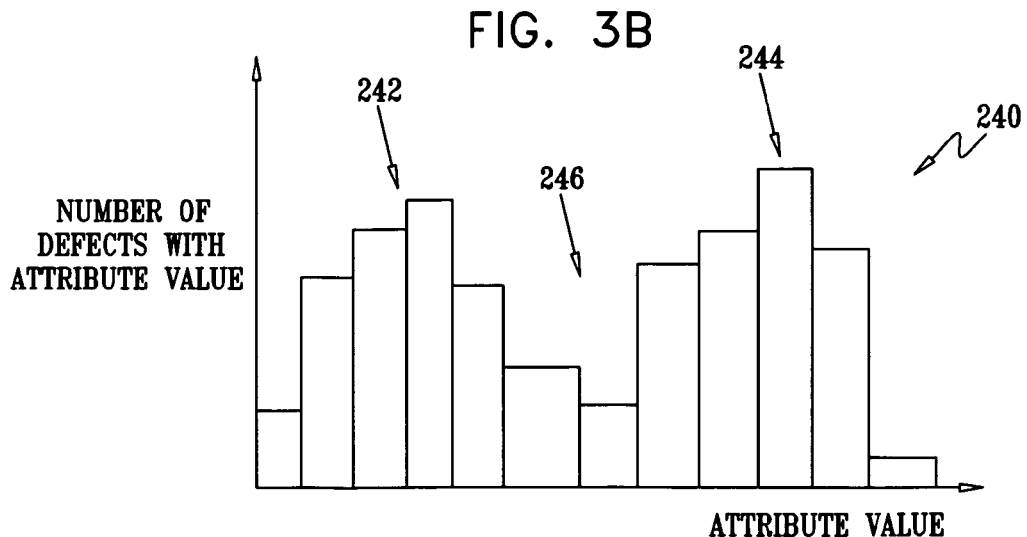

FIG. 3A is a schematic unimodal histogram 250 of an attribute of defects and FIG. 3B is a schematic multimodal histogram 240 of an attribute of defects, according to an embodiment of the present invention. A disclosed embodiment of the present invention uses twelve attributes, which are further described below with reference to Table I. The description herein, for FIGS. 3A and 3B, refers to one generic attribute. Histograms 240 and 250 show the number of defects vs. the attribute value for the defects, where both the number and the attribute values are assumed for the purposes of this explanation to have arbitrary values. Typically, attribute distributions are similar to histogram 250, which has a unimodal distribution.

In some cases the attribute distributions may not be unimodal, for example, if two classes of defects are distinct in attribute space but yet arise from similar population sizes. In such cases, a histogram 240 of the attribute may have a bimodal shape, where a class A of attribute values cluster around value a low value 242 and a class B of attribute values cluster around a high value 244.

The inventor has found that, in attribute space, there are one or more sections of any attribute histogram in which there is a preponderance of the nuisances. For histogram 250, for example, the one or more sections may comprise all or part of a central region 253, and/or all or part of a region outside the central region. For histogram 240, the one or more sections may comprise regions around values 242 and 244. Outside these one or more sections, there is a preponderance of true defects. Thus, for histogram 240, a preponderance of true defects are in a section 246 in a range between values 242 and 244.

Hereinbelow, by way of example, the one or more sections having a preponderance of nuisance values are assumed to comprise central region 253 of histogram 250, which in turn defines histogram tail regions 256 and 258. The regions are delineated by a low threshold 252 and a high threshold 254. Consequently, below the low threshold and above the high threshold, i.e., in histogram tail regions 256 and 258, there is a preponderance of true defects.

Figure 4:
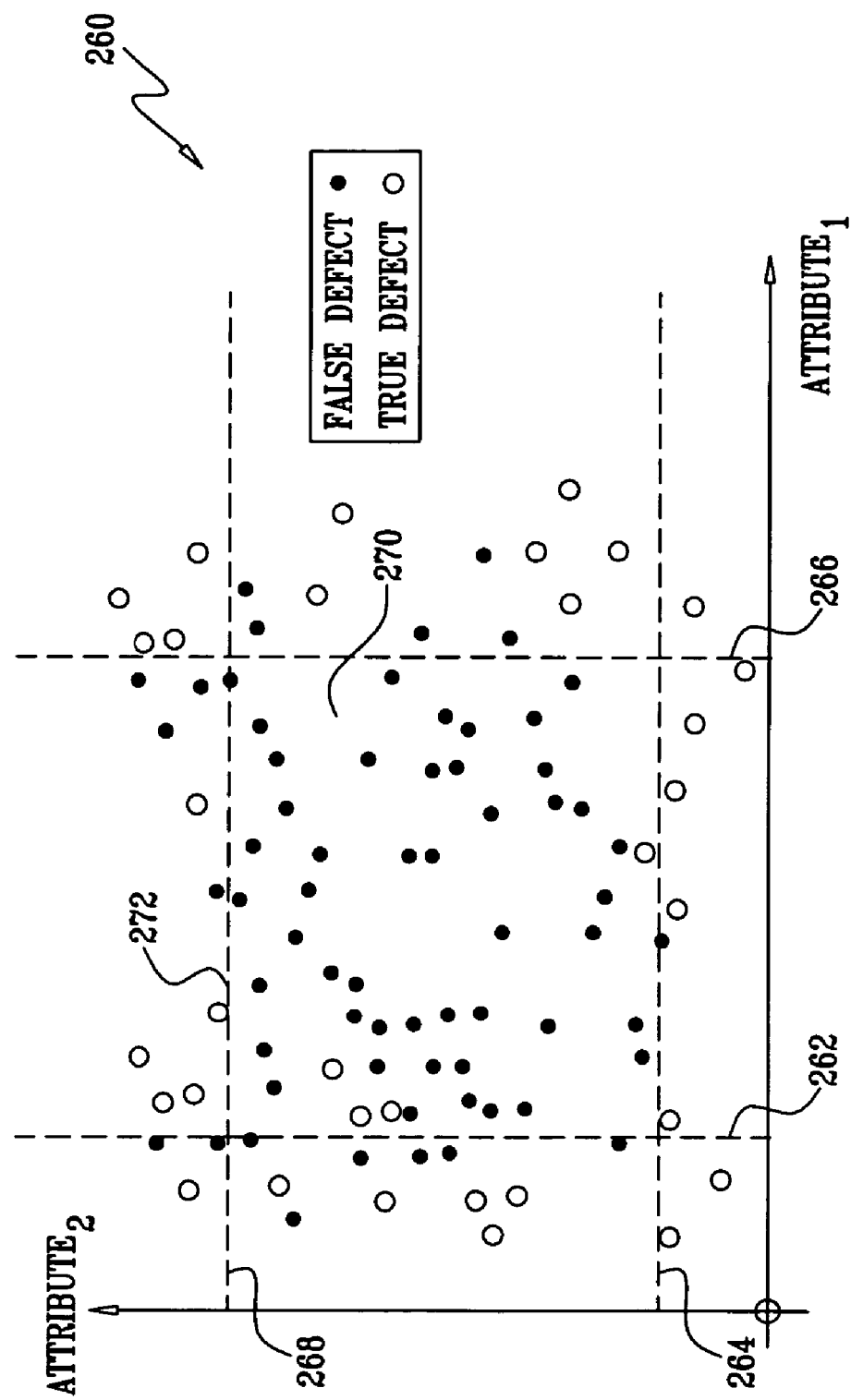
FIG. 4 is a schematic 2-dimensional graph of a first generic attribute and a second generic attribute of defects, according to an embodiment of the present invention.

FIG. 4 is a schematic 2-dimensional graph 260 of a first generic attribute and a second generic attribute of defects, according to an embodiment of the present invention. Each generic attribute is assumed to behave approximately as described above with reference to FIG. 3A, so that each attribute has a respective low threshold 262, 264, and a respective high threshold 266, 268. In a region 270, i.e., within a box 272 defined by the thresholds, defects will comprise a preponderance of nuisance defects, and defects outside the box will comprise a preponderance of true defects. The property exemplified by 2-dimensional graph 260 is amplified herein to apply to an N-dimensional graph of attributes, where N is any natural number.

It will be understood that each threshold value referred to in reference to FIGS. 3A and 4 may typically be chosen from a range of values. A threshold value that is set closer to a mean value of the attribute makes the tail larger; a value set farther from the mean value makes the tail smaller. Typically, as the size of the tail reduces, there is a corresponding increase in the ratio of true defects to nuisances in the tail; however, the reduction in tail size increases the number of true defects that are not in the tail. Embodiments of the present invention select the threshold values so as to optimize the numbers of true defects in the tails of the attribute distribution histograms.

Referring back to step 206 of FIG. 2, operator 90 adjusts the threshold values of each of the attributes to optimize the number of true defects in regions equivalent the region outside box 272 (FIG. 4), while maintaining the number of nuisances as low as possible.

Table I below lists the twelve attributes $Att_n$ calculated for each defect by the disclosed embodiment referred to above, where $1 \leq n \leq 12$, $n \epsilon 1$. The symbols used in Table I are defined and explained in Table II.

TABLE I

| ATTRIBUTE SYMBOL | DEFINITION |
|---|---|
| $Att_1$ | $Log_{10}V$ |
| $Att_2$ | $\frac{1}{4N_{DF}} \sum_{i \epsilon DFalarms} \sum_{j=1}^{4} \Delta GL_i^{(j)}$ |
| $Att_3$ | $\left\| \sum_{i \epsilon DF+ve\ alarms} \sum_{j=1}^{4} Q_j \cdot \Delta GL_i^{(j)} \right\|^{1/2} / \frac{1}{4} \sum_{i \epsilon DF+ve\ alarms} \sum_{j=1}^{4} \Delta GL_i^{(j)}$ |
| $Att_4$ | $\frac{1}{N_{GFU}} \sum_{i \epsilon GFUalarms} \Delta GL_i^{(5)}$ |
| $Att_5$ | $\frac{1}{4N_{GF}} \sum_{i \epsilon GFalarms} \sum_{j=1}^{4} \Delta GL_i^{(j+5)}$ |
| $Att_6$ | $\left\| \sum_{i \epsilon GF+ve\ alarms} \sum_{j=1}^{4} Q_j \cdot \Delta GL_i^{(j+5)} \right\|^{1/2} / \frac{1}{4} \sum_{i \epsilon GF+ve\ alarms} \sum_{j=1}^{4} \Delta GL_i^{(j+5)}$ |
| $Att_7$ | $\frac{1}{4N_1} \sum_{i \epsilon alarms} \left( \sum_{j=1}^{4} GL_i^{(j)}(ref) \right)$ |
| $Att_8$ | $\frac{1}{N_1} \sum_{i \epsilon alarms} GL_i^{(5)}(ref)$ |
| $Att_9$ | $\frac{1}{4 \cdot N_2} \sum_{i \epsilon alarms} \sum_{j=6}^{9} GL_i^{(j)}(ref)$ |
| $Att_{10}$ | $\frac{1}{N_2} \sum_{i \epsilon alarms} GL_i^{(10)}(ref)$ |
| $Att_{11}$ | $\frac{1}{4N_{GF}} \sum_{i \epsilon GF\ alarms} \sum_{j=1}^{4} G_i^{(j+5)} - \frac{1}{4N_{DF}} \sum_{i \epsilon DF\ alarms} \sum_{j=1}^{4} G_i^{(j)}$ |
| $Att_{12}$ | $\frac{1}{N_{GFU}} \sum_{i \epsilon BF\ alarms} \Delta GL_i^{(10)}$ |

In Table I, vertical brackets represent the determinant of the corresponding matrix.

TABLE II

| Notation | Definition |
|---|---|
| V | Number of pixels in a defect |
| $N_1$ | Number of alarms detected by image processor IP1 in a defect |
| $N_2$ | Number of alarms detected by image processor IP2 in a defect |
| $N_{DF}$ | Number of dark field (DF) alarms in a defect |
| $N_{GFU}$ | Number of gray field union (GFU) alarms in a defect |

TABLE II-continued

| Notation | Definition |
|---|---|
| $N_{GF}$ | Number of gray field (GF) alarms in a defect |
| $N_{BF}$ | Number of bright field (BF) alarms in a defect |
| $G_i^{(j)}$ | Grade of pixel i in detector j |
| $GL_i^{(j)}$ (ref) | Reference gray level of detector j in pixel i |
| $\Delta GL_i^{(j)}$ | Inspected gray level - Reference gray level of detector j in pixel i. |
| $Q_j$ | $\begin{bmatrix} 0 & 2x_jy_j \\ 2x_jy_j & 0 \end{bmatrix}$, where $(x_j, y_j)$ is the relative spatial coordinate of the j'th gray level (GL) detector. $j \varepsilon \{1, 2, 3, 4\}, x_j \varepsilon \{1, -1\}, y_j \varepsilon \{1, -1\}$. |

In addition to the twelve attributes shown in Table I, an additional attribute, herein termed the die participation attribute ($Att_{DP}$), is calculated for each defect. A value assigned to $Att_{DP}$ is a value representing the number of other dies for which a defect with corresponding or neighboring die coordinates has been found. The inventor has found that defects with large values of $Att_{DP}$ broadly correspond to nuisance defects, and conversely, defects with small values of $Att_{DP}$ broadly correspond to true defects.

Figure 5:
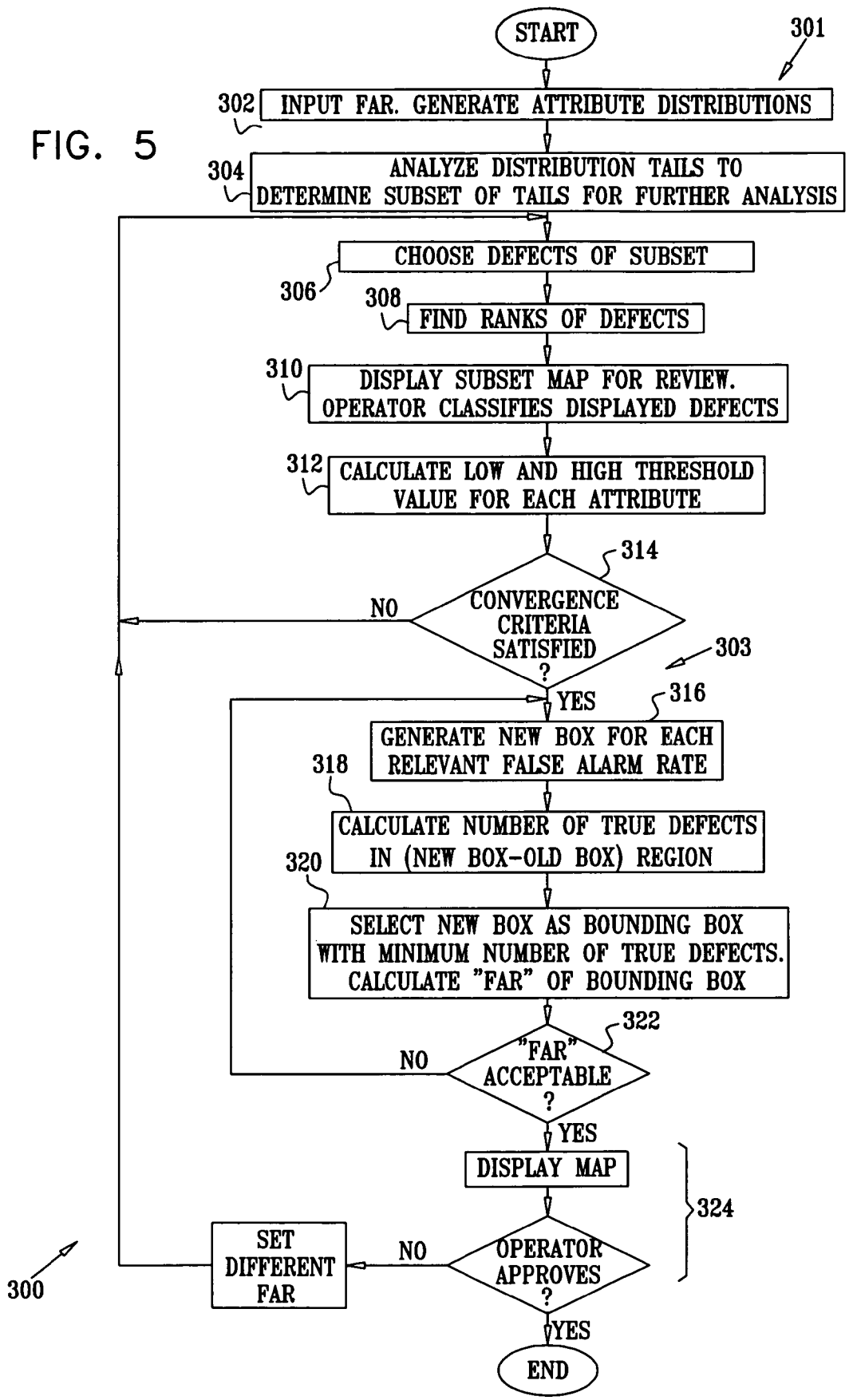
FIG. 5 is a flowchart showing steps performed in a directed review of defects, according to an embodiment of the present invention.

FIG. 5 is a flowchart 300 showing steps performed in a directed review of defects, according to an embodiment of the present invention. Flowchart 300 corresponds to the learning phase described above in reference to step 206 (FIG. 2). In performing the steps of the flowchart, apparatus 10 automatically generates initial thresholds of the attributes listed in Table I having lowest mean values of $Att_{DP}$. These thresholds are then adjusted to form final threshold values for the attributes. Flowchart 300 is divided into two stages, a first uni-dimensional stage 301 wherein each of the attribute distributions are analyzed substantially independently, and a second multi-dimensional stage 303 wherein correlations between the distributions are taken into account.

In a first step 302 of stage 301, operator 90 inputs a value of a prescribed false alarm rate (FAR) that apparatus 10 is to achieve. A typical value for FAR is 0.05, although any other suitable value may be used. Also in the first step, for each attribute post-processor 62 forms a distribution, also herein termed a histogram, of all candidate defects having the attribute. The candidate defects correspond to the defects, typically comprising a large proportion of nuisances, displayed at the conclusion of step 204 (FIG. 2). In an embodiment of the present invention, each histogram is formed to have dynamic bin sizes, the number of bins n being given by expression (1):

$$n = \left\lceil \frac{N - N_{miss}}{N} \cdot \frac{100}{bin\_percentile} \right\rceil \quad (1)$$

where N is the total number of defects having the attribute; $N_{miss}$ is the number of defects without the attribute; and bin_percentile is a constant between 1 and 100, a typical value for the constant being of the order of 7.

For example, assuming that bin_percentile=5, an attribute that is defined for all defects, so that $N_{miss}=0$, is sorted into 20 bins; an attribute that is defined for 7% of the defects, so that $$\frac{N - N_{miss}}{N} = 0.07,$$

is sorted into two bins, and an attribute defined for less than 5% of the defects, so that $$\frac{N - N_{miss}}{N} < 0.05,$$

is placed in one bin.

The bin borders $[x^{(1)}, x^{(2)}, x^{(3)}, \ldots, x^{(n)}, x^{(n+1)}]$ are given by expression (2):

$$\begin{cases} x^{(1)} = x_{min} \\ x^{(i)} = x\left(\frac{100(i-1)}{n}\right) \forall\, 1 < i \le n \\ x^{(n+1)} = x_{max} \end{cases} \quad (2)$$

where $x_{min}$ is the minimum value of the attribute;
$x_{max}$ is the maximum value of the attribute; and
x(p) is the p'th percentile of the attribute x.

In a second step 304, tails of each of the histograms are analyzed. For each tail, a mean value $\overline{Att_{DP}}$ of the die participation attribute of all the defects in the tail is calculated, and the $K_{chosen}$ tails having the lowest values of $\overline{Att_{DP}}$ are reviewed further. $K_{chosen}$ is any number greater than zero; a typical value for $K_{chosen}$ is 5.

For each histogram, each tail is assumed to comprise m extreme bins of the histogram, where m is defined according to expression (3):

$$m = \left\lceil \frac{N_{rev}}{N_{class}} \right\rceil \quad (3)$$

where $N_{rev}$ is a number, greater than 1, of the total number of defects chosen for review for this attribute. A typical value for $N_{rev}$ is 8; and
$N_{class}$ is a number, greater than 1, of classified defects per bin. A typical value for $N_{class}$ is 6. $N_{class}$ represents a minimum number of defects of a bin to be reviewed.

The steps following step 304 are typically iterated, as is explained in more detail below.

In a third step 306, in a first iteration, each tail selected according to step 304 has a subset of $N_{rev}$ defects chosen from the bins of its tail. Thus, using the typical values given above with respect to equation (3), in the first iteration six defects from the most extreme bin and two defects from the next-most extreme bin are reviewed. In any subsequent iteration, rather than opening m bins from the extremities of the attributes, bins within the threshold values determined in step 312 below, and that do not have $N_{class}$ classified defects, are opened so as to provide further subsets of defects for classification. Typically, for a given iteration sampling a low tail, the number of bins opened is bounded from above by the number of bins up to the current low threshold. A generally similar limitation applies to sampling the high tail.

In a fourth step 308, the defects to be reviewed are selected according to a ranking system that post-processor 62 applies to the defects. Defects that are as yet unclassified (according to step 310 below) are assigned a numerical rank equal to the number of tail bins, of the different attributes, they fall into. The tail bins are those bins selected in step 306 above. Defects with higher numerical ranks are selected first. It will be understood that the rank assigned to a particular defect may change as the process of flowchart 300 iterates, since the tail bins upon which the ranking depends may change according to step 306.

In a fifth step 310, the defects selected for review in step 308 are displayed on monitor 64 for review by operator 90. The operator classifies the displayed defects as true, nuisance, or unknown, and post-processor 62 uses the classification in subsequent steps of flowchart 300. Alternatively or additionally, locations of the selected defects may be sent to another tool, for example an electron microscope, so that the defects may be reviewed using the tool. This method is advantageous for defects that may be too small to be manually classified using optical methods.

In a sixth step 312, after operator 90 has performed the classification of all the chosen tails, post-processor 62 calculates a lower threshold value $T_{lo}$ and an upper threshold value $T_{hi}$ for each of the attributes. The calculation is based on the prescribed false alarm rate (FAR) input in step 302.

$T_{lo}$ is the maximum value of T for which the following criterion is correct:

$$\frac{N_f(T)}{N_f(T)+N_t(T)} < FAR^{(1D)} \qquad (4)$$

where $N_f(T)$ is the number of classified nuisances with an attribute value <T;

$N_t(T)$ is the number of classified true defects with an attribute value <T; and $FAR^{(1D)}$ is a number less than 1, corresponding to a multiple of FAR. A typical value for $FAR^{(1D)}$ is 3×FAR.

$T_{hi}$ is the minimum value of T for which the criterion of expression (4) is correct, with the following redefined variables:

$N_f(T)$ is the number of classified nuisances with an attribute value >T; and $N_t(T)$ is the number of classified true defects with an attribute value >T.

In a convergence step 314, which is the last step in stage 301, post-processor 62 checks to see that numbers of defects that have been reviewed are sufficient, in other words, that at least a minimum number $N_{class}$ of defects have been reviewed in each tail bin. To perform this check, in a disclosed embodiment, in each of the $K_{chosen}$ chosen tails, bins of each of the respective histograms are checked according to the following criteria:

For the low tail $T_{lo}$:

$$N_{rev}^{(b)} \geq N_{class} \forall\ b \leq b_0 \qquad (5)$$

For the high tail $T_{hi}$:

$$N_{rev}^{(b)} \geq N_{class} \forall\ b \geq b_0 \qquad (6)$$

where $N_{rev}^{(b)}$ is the total number of reviewed and classified defects in bin b, and $b_0$ is the bin which includes T.

Post-processor 62 checks that expressions (5) and (6) are satisfied for all chosen tails. If the expressions are satisfied, the post-processor continues to multidimensional stage 303. If the expressions are not all satisfied, post-processor 62 suggests to operator 90 that an additional iteration of directed review, comprising a repetition of steps 306-314, be performed.

The $T_{lo}$ and $T_{hi}$ levels determined in stage 301 may be visualized as forming an N-dimensional box, where in the example described herein N is 12. The N-dimensional box corresponds to 2-dimensional box 272 described in reference to FIG. 4. Within the N-dimensional box there are a preponderance of nuisance defects; outside the box there are a preponderance of true defects. The N-dimensional box is herein also referred to as the first-stage box.

In multidimensional stage 303, post-processor 62 adjusts the threshold values calculated in uni-dimensional stage 301, by taking account of correlations between the attributes for specific defects. The adjustments correspond to expanding the N-dimensional first-stage box. The inputs for stage 303 comprise the set of thresholds $\{T_{lo}, T_{hi}\}$ determined in stage 301, and the manually classified defects that were so classified in that stage, but that lie outside the N-dimensional first-stage box. The adjustment is typically uni-directional, i.e., each $T_{lo}$ is only lowered, and each $T_{hi}$ is only raised, so that the size of a respective tail is reduced. The adjustment thus corresponds to expanding the first-stage box, and it is performed substantially automatically by post-processor 62.

In a first step 316 of stage 303, post-processor 62 considers each of the false alarm defects individually lying outside the N-dimensional first-stage box formed in stage 301. For each of these false alarms, post-processor 62 forms the smallest new box that encloses the first-stage box and the specific false alarm. The sides of each new box are given by expression (7):

$$\hat{T}_{lo}^{(i)} = \min(T_{lo}^{(i)}, att_i^{(fa)}) \text{ and } \hat{T}_{hi}^{(i)} = \max(T_{hi}^{(i)}, att_i^{(fa)}) \forall\ i \qquad (7)$$

where $\hat{T}_{lo}^{(i)}, \hat{T}_{hi}^{(i)}$ are the lower and upper threshold boundaries of the new box, $T_{lo}^{(i)}, T_{hi}^{(i)}$ are lower and upper threshold boundaries of the first-stage box, and $att_i^{(fa)}$ is the value of the attribute of the specific false alarm, for the $i^{th}$ attribute.

In a step 318, for each new box generated in step 316, post-processor 62 calculates the number of true defects, $\Delta N_T$, which are in the new box but not in the corresponding first-stage box, using expression (8):

$$\hat{T}_{lo}^{(i)} \leq att_i^{(true)} < T_{lo}^{(i)} \text{ or } T_{hi}^{(i)} < att_i^{(true)} \leq \hat{T}_{hi}^{(i)} \text{ for any } i \qquad (8)$$

where $att_i^{(true)}$ is the value of the attribute of the true defect for the $i^{th}$ attribute.

In a step 320, post-processor 62 chooses the new box having the minimum value of $\Delta N_T$ as the box to be used in filtering nuisances, this box herein being termed the bounding box. The false alarm rate of the bounding box, $FAR_{bb}$, is given by expression (9):

$$FAR_{bb} = \frac{N_{FA}(T)}{N_{FA}(T) + N_T(T)} \qquad (9)$$

where T represents the set of thresholds for the bounding box, $N_{FA}(T)$ is the number of false alarms determined by the box, i.e., outside the box, and $N_T(T)$ is the number of true defects determined by the box.

In a decision step 322, post-processor checks to see that the number of false alarms outside the bounding box is sufficiently small, using expression (10):

$$N_{FA}(T) < \max(N_{FA}^{(max)}, FAR^{(recipe)} \cdot (N_T(T) + N_{FA}(T))) \qquad (10)$$

where $N_{FA}^{(max)}$ is a number, $\geq 0$, which ensures that flowchart 300 gives satisfactory results when small numbers of defects are reviewed. A typical value of $N_{FA}^{(max)}$ is 4. $FAR^{(recipe)}$ is the prescribed false alarm rate that is to be produced by flowchart 300.

If expression (10) is not satisfied, steps 316, 318, and 320 of the multidimensional stage are reiterated.

Satisfaction of expression (10) concludes the multidimensional stage, giving a final bounding box having a set of thresholds $T=\{T_{fbb}\}$.

In optional steps 324, post-processor 62 may display on monitor 64 a map of the true defects determined by the final bounding box, and $\{T_{fbb}\}$ may be approved or rejected by operator 90 on the basis of the display. If the display is approved, $\{T_{fbb}\}$ is used in analysis of production wafers in substantially the same stage of fabrication as wafer 22; if the display is rejected, process 300 may be repeated using a different value of FAR as the false alarm rate to be achieved by the process.

While the process described above has assumed, by way of example, that only one wafer is used to determine $\{T_{fbb}\}$, it will be appreciated that more than one wafer may be used, such wafers typically being in substantially the same stages of fabrication. Alternatively or additionally, the same wafer may be re-analyzed to give an additional set of distributions. Typically, the multiple sets of results derived by either or both these methods may be applied to find $\{T_{fbb}\}$ in a cumulative and/or an iterative fashion. It will also be appreciated that such a cumulative application may also be used to add, delete, or alter attributes from those used in an initial analysis of a wafer.

In one embodiment of the present invention, modifications to $\{T_{fbb}\}$ are performed after two wafers in substantially the same stage of fabrication are analyzed, when there has been a process variation between the two wafers. In this case, typically the uni-dimensional and multidimensional stages of flowchart 300 are applied to the first wafer, but only the multidimensional stage of flowchart 300 is applied to the second wafer.

It will be understood that the number of attributes used in embodiments of the present invention is not limited to a specific number such as the twelve attributes of the embodiment described above. Substantially any convenient number of attributes may be used, the number typically being chosen according to the detectors and/or the configuration of apparatus 10. It will also be understood that the attributes described herein are exemplary, and that other attributes, generally similar to those described herein and enabling false alarms to be distinguished from true defects, may be used in embodiments of the present invention.

It will further be understood that the scope of the present invention includes distinguishing between classes of defects, such as those exemplified in the Background of the Invention, as well as distinguishing false alarms from true defects. Distinguishing between classes of defects may be accomplished by selection of relevant attributes, and using these attributes in the processes described above with respect to FIGS. 2 and 5.

It will also be understood that the detectors from which the attributes are generated may comprise substantially any type of detector or detecting system that generates a signal in response to scanning of wafer 26. For example, a detecting system for an electromagnetic radiation scanning system may comprise detectors that are at least partly based on far field scattered radiation from wafer 26, and/or on characteristics of returning radiation such as wavelength, amplitude, phase and/or polarization of the radiation. For scanning systems that comprise charged particle scanning, detectors based on substantially any measurable parameter of charged particle returning from wafer 26 may be used. Such parameters include, but are not limited to, the number, velocity and/or the energy of the charged particles.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

I claim:

1. A method for inspecting a sample, comprising:
receiving, by a processor, an image of the sample from an imaging system;
receiving, by the processor, a definition of image attributes that are characteristic of defects;
processing, by the processor, an image of the sample so as to identify candidate defects on the sample;
forming, by the processor, distributions of values of the respective attributes from the candidate defects;
selecting, by the processor, a set of the candidate defects that are characterized by respective candidate attribute values that fall in one or more tails of the distributions;
presenting, by the processor via a monitor, the selected set to a human operator;
receiving from the operator, by the processor via a computing system, respective classifications of the candidate defects in the selected set, wherein the defects may be classified as at least one of a true defect and a false alarm defect; and
iteratively refining, by the processor, a definition of the one or more tails of the distributions responsively to the classifications until a criterion of a false alarm rate is met.

2. The method according to claim 1, wherein the one or more tails comprise a plurality of tails, and wherein refining the definition comprises refining a threshold of each of the plurality of tails independently of each other.

3. The method according to claim 1, wherein the one or more tails comprise a plurality of tails, and wherein refining the definition comprises refining a threshold of each of the plurality of tails responsively to each other.

4. The method according to claim 1, wherein the one or more tails comprise a plurality of tails, and wherein the set of the candidate defects comprises respective subsets of the candidate defects, and wherein refining the definition comprises refining the definition of each of the plurality of tails in response to the classifications of the candidate defects in each of the subsets.

5. The method according to claim 1, wherein iteratively refining the definition comprises iteratively repeating the steps of selecting the set, presenting the selected set, and refining the definition.

6. The method according to claim 1, wherein iteratively refining the definition comprises changing the definition so that a size of the one or more tails is reduced.

7. The method according to claim 1, wherein inspecting the sample comprises inspecting the sample using at least one of electromagnetic radiation and charged particles.

8. The method according to claim 1, and comprising using the refined definition for automatic inspection of at least one of the sample and one or more further samples.

9. The method according to claim 1, wherein the candidate defects comprise two or more classes of defects, and wherein refining the definition of the one or more tails comprises refining the definition so as to distinguish between the two or more classes.

10. An apparatus for inspecting a sample, comprising:
an imaging system which generates an image of the sample; and a processor which is adapted to: receive the image of the sample from the imaging system; receive a definition of image attributes that are characteristic of defects, process the image so as to identify candidate defects on the sample, form distributions of values of the respective attributes from the candidate defects, select a set of the candidate defects that are characterized by respective candidate attribute values that fall in one or more tails of the distributions, present the selected set to a human operator, receive from the operator respective classifications of the candidate defects in the selected set via a computing system, wherein the defects may be classified as at least one of a true defect and a false alarm defect; and
iteratively refine a definition of the one or more tails of the distributions responsively to the classifications until a criterion of a false alarm rate is met.

11. The apparatus according to claim 10, wherein the one or more tails comprise a plurality of tails, and wherein refining the definition comprises refining a threshold of each of the plurality of tails independently of each other.

12. The apparatus according to claim 10, wherein the one or more tails comprise a plurality of tails, and wherein refining the definition comprises refining a threshold of each of the plurality of tails responsively to each other.

13. The apparatus according to claim 10, wherein the one or more tails comprise a plurality of tails, and wherein the set of the candidate defects comprises respective subsets of the candidate defects, and wherein refining the definition comprises refining the definition of each of the plurality of tails in response to the classifications of the candidate defects in each of the subsets.

14. The apparatus according to claim 10, wherein iteratively refining the definition comprises iteratively repeating the steps of selecting the set, presenting the selected set, and refining the definition.

15. The apparatus according to claim 10, wherein iteratively refining the definition comprises changing the definition so that a size of the one or more tails is reduced.

16. The apparatus according to claim 10, wherein the imaging system uses at least one of electromagnetic radiation and charged particles to generate the image.

17. The apparatus according to claim 10, and wherein the apparatus is adapted to use the refined definition for automatic inspection of at least one of the sample and one or more further samples.

18. The apparatus according to claim 10, wherein the candidate defects comprise two or more classes of defects, and wherein refining the definition of the one or more tails comprises refining the definition so as to distinguish between the two or more classes.

19. A method for inspecting a sample, comprising:
at an image processing system coupled to an imaging system, receiving an image of the sample from the imaging system, identifying a set of candidate defects included in the sample using the image, selecting one or more attributes from a predefined set of attributes for each defect in the identified set of candidate defects, calculating one or more defect attribute values for each selected attribute, and defining a subset of attributes, wherein the subset includes at least one of the attributes included in the predefined set of attributes;
calculating, for each attribute included in the defined subset of attributes, a low threshold value and a high threshold value, thereby generating a set of thresholds corresponding to the defined subset of attributes;
selecting, by the image processing system and based on the calculated attribute value of each defect and the low threshold value and high threshold value of each attribute, a plurality of the candidate defects from the set of candidate defects for manual classification, and presenting, via a monitor, the selected candidate defects for review by a human operator;
receiving, by the image processing system, a labeling for each candidate defect in the selected set of candidate defects, wherein labels correspond to at least one of a true defect, a false alarm defect, and an unknown defect;
automatically adjusting at least one threshold value in the set of threshold values, based on the labeling, and repeatedly refining the set of threshold values according to manual classifications of candidate defects presented for review until a convergence criterion is met; and
providing a set of final threshold values associated with the convergence criterion and corresponding to the predefined set of attributes to a defect classifier.

20. The method according to claim 19, further comprising calculating a die participation attribute for each candidate defect.

21. The method according to claim 20, wherein the defining of the subset of attributes is based on the die participation attribute.

22. The method according to claim 19, further comprising:
generating a distribution of calculated attribute values based on the set of threshold values, wherein the false alarm defects are found in a tail of the distribution.

23. The method according to claim 19, wherein the convergence criterion is met when a minimum number of defects have been presented to the human operator.

24. The method according to claim 19, wherein inspecting the sample comprises inspecting the sample using at least one of electromagnetic radiation and charged particles.

25. An apparatus for inspecting a sample, comprising:
an imaging system configured to generate an image of the sample; and
an image processing system coupled to receive the image from the imaging system and to:
identify a set of candidate defects included in the sample using the image, select one or more attributes from a predefined set of attributes for each defect in the identified set of candidate defects, calculate one or more defect attribute values for each selected attribute, and define a subset of attributes, wherein the subset includes at least one of the attributes included in the predefined set of attributes;

calculate, for each attribute included in the defined subset of attributes, a low threshold value and a high threshold value, thereby generating a set of thresholds corresponding to the defined subset of attributes;

select, based on the calculated attribute value of each defect and the low threshold value and high threshold value of each attribute, a plurality of the candidate defects from the set of candidate defects for manual classification, and present, via a monitor, the selected candidate defects for review by a human operator;

receive a labeling for each candidate defect in the selected set of candidate defects, wherein labels correspond to at least one of a true defect, a false alarm defect, and an unknown defect;

automatically adjust at least one threshold value in the set of threshold values, based on the labeling, and repeatedly refine the set of threshold values according to manual classifications of candidate defects presented for review until a convergence criterion is met; and provide a set of final threshold values associated with the convergence criterion and corresponding to the predefined set of attributes to a defect classifier.

26. The apparatus of claim 25, wherein the image processing system is further adapted to calculate a die participation attribute for each candidate defect.

27. The apparatus of claim 26, wherein the defining of the subset of attributes is based on the die participation attribute.

28. The apparatus of claim 25, wherein the image processing system is further adapted to generate a distribution of calculated attribute values based on the set of threshold values, wherein the false alarm defects are found in a tail of the distribution.

29. The apparatus of claim 25, wherein the convergence criterion is met when a minimum number of defects have been presented to the human operator.

30. The apparatus of claim 25, wherein the imaging system uses at least one of electromagnetic radiation and charged particles to generate the image.

* * * * *